(12) United States Patent
Hildebrandt et al.

(10) Patent No.: US 8,826,728 B1
(45) Date of Patent: Sep. 9, 2014

(54) PLATE TYPE DIRECT REFRIGERATION

(75) Inventors: Marc J. Hildebrandt, Midland, MI (US); Theodore W. Selby, Midland, MI (US); Christopher John Rudy, Fort Gratiot, MI (US)

(73) Assignee: King Refrigeration, Inc., Midland, MI (US)

( * ) Notice: Subject to any disclaimer, the term of this patent is extended or adjusted under 35 U.S.C. 154(b) by 2634 days.

(21) Appl. No.: 11/827,505

(22) Filed: Jul. 12, 2007

Related U.S. Application Data

(60) Provisional application No. 60/830,514, filed on Jul. 13, 2006.

(51) Int. Cl.
*G01N 11/00* (2006.01)
(52) U.S. Cl.
USPC .......................................................... 73/54.43
(58) Field of Classification Search
USPC .......................................................... 73/54.43
See application file for complete search history.

(56) References Cited

U.S. PATENT DOCUMENTS

| | | | |
|---|---|---|---|
| 5,167,275 A | 12/1992 | Stokes et al. | 165/109.1 |
| 5,503,002 A | 4/1996 | Selby et al. | 73/54.28 |
| 5,636,685 A * | 6/1997 | Gawve et al. | 165/109.1 |
| 6,306,658 B1 | 10/2001 | Turner et al. | 436/37 |
| 6,755,044 B1 | 6/2004 | Hildebrandt | 62/276 |
| 6,786,081 B1 | 9/2004 | Hildebrandt et al. | 73/54.43 |
| 7,043,968 B1 | 5/2006 | Hildebrandt et al. | 73/54.28 |

OTHER PUBLICATIONS

ASTM D 4684-98, Aug. 1998.
Hildebrandt et al., U.S. Appl. No. 10/929,828, filed Aug. 30, 2004.
Hildebrandt et al., U.S. Appl. No. 60/830,514, filed Jul. 13, 2006.

* cited by examiner

*Primary Examiner* — Peter Macchiarolo
*Assistant Examiner* — Alex Devito
(74) *Attorney, Agent, or Firm* — Christopher John Rudy (57) ABSTRACT

Refrigerant gas can pass through hollow type plate, and this can be employed for refrigeration of a block by employment of the plate in thermal communication with the block. The block, which typically contains one or more test cells, may have a rhomboid shape.

20 Claims, 7 Drawing Sheets

PLATE TYPE DIRECT REFRIGERATION

This claims benefits under 35 USC 119(e) of U.S. provisional patent application No. 60/830,514 filed on Jul. 13, 2006 A.D. The specification of that application is incorporated herein by reference in its entirety.

FIELD AND PURVIEW OF THE INVENTION

This concerns refrigeration by employing a hollow type plate through which refrigerant gas passes, which can be in thermal communication with a block. The block may have any shape, but a rhomboid shape is a proven shape that can be beneficially used. The same can be employed in instrumentation for oil testing.

BACKGROUND TO THE INVENTION

Hildebrandt et al., U.S. Pat. No. 6,786,081 B1, discloses direct and/or opposing flow path refrigeration, and Hildebrandt et al., U.S. Pat. No. 7,043,968 B1, discloses a directly refrigerated block. The devices of these patents can be beneficially employed in ASTM D 4684 type testing. See also, Selby et al., U.S. Pat. No. 5,503,002 A1; Hildebrandt, U.S. Pat. No. 6,755,044 B1; and Hildebrandt et al., U.S. patent application Ser. No. 10/929,898. Note, U.S. Pat. No. 5,167,275 A1 to Stokes et al., and U.S. Pat. No. 6,306,658 B1 to Turner et al.

Such art, however, is not without shortcoming, especially in light of desires to provide data with higher accuracy, precision and uniformity, ever more quickly, in the demanding and rapidly evolving field of oil testing. This applies, in particular, to cell-to-cell temperature control in directly refrigerated blocks employed in instrumentation for MRV/TP-1 type gang testing.

A FULL DISCLOSURE OF THE INVENTION

In general, the present invention provides a hollow type plate through which refrigerant gas passes, which can be employed for refrigeration of a block by employment of the plate in thermal communication with the block. The block, which typically contains one or more test cells, may have a rhomboid shape.

The invention is useful in refrigeration and oil testing.

Significantly, by the invention, the art is advanced in kind. Direct refrigeration is brought to higher levels of performance, especially in laboratory instrumentation for testing of oils and other lubricants and fluids, whether oleaginous or nonoleaginous. In particular, block design and manufacture can be simplified, as internal refrigerant passageways and "wedges" can be avoided in the block. Instead, a hollow type plate can be placed in thermal contact with the block, and refrigeration occurs by passing the refrigerant gas through the plate, which then cools the block. As well, internal heater channels can be avoided in the block, further simplifying its construction, and rendering it even more uniform with respect to thermal conduction. Instead, if desired, a heating element can be placed outside the block, for instance, sandwiched between the block and an externally placed hollow type plate. A rhomboid shaped block may be advantageously employed, especially for instrumentation for MRV/TP-1 and ASTM D 4684 type testing. Among advantages also can be mentioned highly accurate, precise and uniform temperature control provided hereby.

Numerous further advantages attend the invention.

The drawings form part of the specification hereof. With respect to the drawings, which are not necessarily drawn to scale, the following is briefly noted:

FIG. 7 is a top plan view of a rhomboid block as from the ensemble of FIG. 6 but in a mirror image configuration as for production, with individual test cells identified by number.

FIGS. 8 and 9 are top plan views of embodiments of the invention, with their blocks having test cells in linear arrays.

FIG. 10 et seq. are views of another embodiment hereof.

FIG. 10 shows a rhomboid evaporator device for TP-1 testing, with FIG. 10A an exploded top view without its insulation, and FIG. 10B an exploded front perspective view without its evaporator features.

FIG. 11 shows the spacer from the device of FIG. 10A, with FIG. 11A a side view, and FIG. 11B a front view.

FIG. 12 shows the heater from the device of FIG. 10A.

FIG. 13 shows the back plate from the device of FIG. 10A, with FIG. 13A a front, inside view, and FIG. 13B a side view.

FIG. 14 is an exploded view of the evaporator unit in the device of FIG. 10A.

FIG. 15 shows the front plate from the device of FIG. 10A, with FIG. 15A a front view, and FIG. 15B a side view.

FIG. 16 shows the lower insulation block from the device of FIG. 10B, with FIG. 16A a top view, FIG. 16B a side view, and FIG. 16C a front view.

FIG. 17 shows the upper insulation block from the device of FIG. 10B, with FIG. 17A a top view, FIG. 17B a side view, and FIG. 17C a front view.

FIG. 18 shows an air delivery system in the upper insulation block of FIG. 17, with FIG. 18A a top view, and FIG. 18B a side view.

FIG. 19 shows the block from the device of FIGS. 10A and 10B, with FIG. 19A a rear view, FIG. 19B a right side view, FIG. 19C a top view, FIG. 19D a front view, and FIG. 19E a left side view.

The invention can be further understood by the detail set out below, which may be read in view of the drawings. The same is to be taken in an illustrative and not necessarily limiting sense.

In the practice of the present invention, a hollow type plate is provided, through which refrigerant gas passes. The plate can assume any suitable shape. For instance, it may be substantially flat and rectangular, flat and square, flat and triangular, flat and elliptical, flat and circular; semicylindrical; semiconic; hemispherical; cylindrical; conic; cuplike; L-shaped; S-shaped; and so forth. Any suitable material can be employed to make up the plate. For instance, it may be of copper, silver, gold, aluminum, iron, alloys with these, and so forth. Refrigeration in the plate may be considered to be direct refrigeration. It is preferred, nonetheless, to introduce the refrigerant gas in a liquid state with introduction from a capillary tube occurring outside the plate per se, say, in a manifold or just before entry into a manifold that is in communication with the inside of the hollow plate, which has a benefit of avoiding exaggerated cold spots where a rapid change in state from liquid to gaseous states (flashing) occurs. The liquid changes to gas in the evaporator.

The hollow type plate can be in thermal communication with a block. The block can assume any suitable shape. For instance, the block can have a rhomboid shape, especially when taken from a top or bottom view; it may have a rhombus shape; or it may be substantially square or rectangular; triangularly, pentagonally or hexagonally prismatic; tetrahedral; semicylindrical or cylindrical; annular; spherical or hemispherical; conical; serpentine; and so forth. Any suitable material can be employed to make up the plate. For instance, it may be of aluminum, copper, silver, gold, iron, alloys with these, and so forth.

Test cells typically are provided in the block, and these may be provided in any suitable array. For example, they may follow a rhomboid, linear, rectangular or square, triangular, pentagonal or hexagonal, semiannular or annular arrangements, and so forth. A rhomboid array can provide for excellent temperature control and many test ports in a small footprint device; a linear array may provide for simple, even flux, and excellent temperature control. A block may contain only one test cell, for example, centered in relation to the outer boundaries of the block.

One or more heaters may be employed for temperature control. Such can be of any suitable shape or variety, and can be employed at any suitable location. For instance, a plurality of thin film electric heating elements can be employed, say, in an array.

A temperature sensor can be employed. Such can be of any suitable shape or variety, and be employed at any suitable location. For instance, a thermocouple may be employed as the temperature sensor, say, vertically in the center of the block.

A device including such components as the foregoing can be employed in instrumentation for motor oil testing. For instance, the device may be a TP-1 device for ASTM D 4684 type testing.

Any suitable refrigerant can be employed. For example, the refrigerant can be R-507 refrigerant.

With respect to the drawings, device ensemble 100 is a TP-1 evaporator type device. It includes block 10, hollow type plate 15 for refrigeration, and heater 40.

The block 10 can be equipped with side mounting brackets 10B and mounting fasteners 10F, for example, screws that are threaded directly into the block 10; has top 10T and a rhomboid box shape; is made of 6061-T6 aluminum; and includes cylindrical test wells 11, which may be of stainless steel, into which test sleeves 12 can be inserted. A well 11 may have sleeve stop-engaging hole 11H. A sleeve 12, which can be of #304 stainless steel and hold the test samples and act as stators in viscosity/rheology testing, can have bottom 12B, generally cylindrical wall, carbide-tipped radius pin 12P, outside pin-type stop 12S that engages the hole 11H and keeps the sleeve 12 from rotating, and flat outside wall portion 12W for relieving air pressure upon insertion and withdrawal of the sleeve 12. Support holes 13 can be provided in the block 10 and tapped for supports for top plates (not illustrated) for securing a plurality of the rotors 20, each of which may have a shaft 21, say, of #304 stainless steel, with top bearing 21B and heat-impeding neck 22; press fit cylindrical drum 23, say, of DELRIN plastic; and radial cup 24, say, of solid carbide, for resting and rotating on the pin 12P. Central hole 14 can be provided in the block 10 for the temperature sensor 30, which is a thermocouple temperature probe.

The hollow type plate 15 is in a form of a flat plate, which may be planar or otherwise contoured, say, to the configuration of the outer boundary of the sides of the block 10, and is in thermal communication with the block 10. A pair of plates 15, each of which is essentially equivalent to the other, is provided on opposing long sides of the block 10. The plate 15 can be made of two components, back component 15B, which is made of copper and includes exit/entry ports 15E, each, for example, having the same size 0.094-inch radius internal passageway, and which includes construction/mounting hole locations 15H; and front component 15F, which is made of copper also, and includes actual construction/mounting holes 15H' that register with the locations 15H of the back component 15B, for example, about twenty smaller holes for soldering and two (or four in another, earlier embodiment) larger holes for mounting. The plate components 15B, 15F can be machined to be mirror images of each other and aligned. Hot solder may be bled into the holes 15' during manufacture of the plate 15. The back component 15B is ¼ of an inch (0.250") thick (in another embodiment ⅛ of an inch (0.125") thick) and has passageway grooves 15P, which are ⅛ of an inch (0.125") deep (in another embodiment ¹⁄₁₆ of an inch (0.0625") deep) and defined by upraised ribs 15R that retain a 0.250" thickness (in another embodiment a 0.125" thickness); it has a flat outside wall surface. The front component 15F is 0.0625" thick, and has flat inside and outside wall surfaces. Although one plate component 15F has a flat inner surface, both components 15B, 15F could have contoured inner surfaces and be attached. The back and front components 15B, 15F are connected in registry and secured together, for example, by silver soldering, which may leave seam 15S and plug the small holes 15H with solder, and copper tubes, say, ³⁄₁₆" in diameter, can be silver brazed to provide the ports 15E, to make the plate 15. In operation, refrigerant gas enters one or more of the ports 15E, courses through the passageway 15P, and leaves through the remaining port or ports 15E that is or are not occupied with gas entry. For example, entry of the refrigerant gas can be carried out through two more distal ports 15E with exit through a central port 15E. Manifold 16 may be employed in conjunction with this. Surprisingly, the flat plate 15 can withstand an enormous amount of pressure, say, up to 7,500 pounds total force or more of refrigerant gas or any pressurized gas at up to 500 pounds per square inch (psi) or more, which is essential when refrigerant gas or other pressurized gas courses through the grooves 15P.

The heater 40 is in a form of a thin film electric heating element. Beneficially, it is provided in an array of a plurality of smaller heating elements, for example, in a side by side array having left and right banks, with each bank including uppermost heater 40A, upper middle heater 40B, lower middle heater 40C, and lowermost heater 40D. Each of the heaters 40A, 40B, 40C and 40D can have a 30-watt output and have a 1-inch height and 3-inch length, for example, as a thin film KAPTYN electric heater, and these can be controlled together. Individual control of a heater 40 may also be carried out. Advantageously, the heater 40 array is placed for mounting between the side wall of the block 10 and the refrigeration plate 15. A thermal paste may be employed.

The device 100 can be insulated with any suitable insulation 50. For example, SYNTAC insulation may be employed as the insulation 50, which, in practice, surrounds the entire block, top, sides and bottom, and other components of the ensemble, with access openings provided for the test ports 11/12 and so forth, of course.

Figures 1, 2, 3, 4:
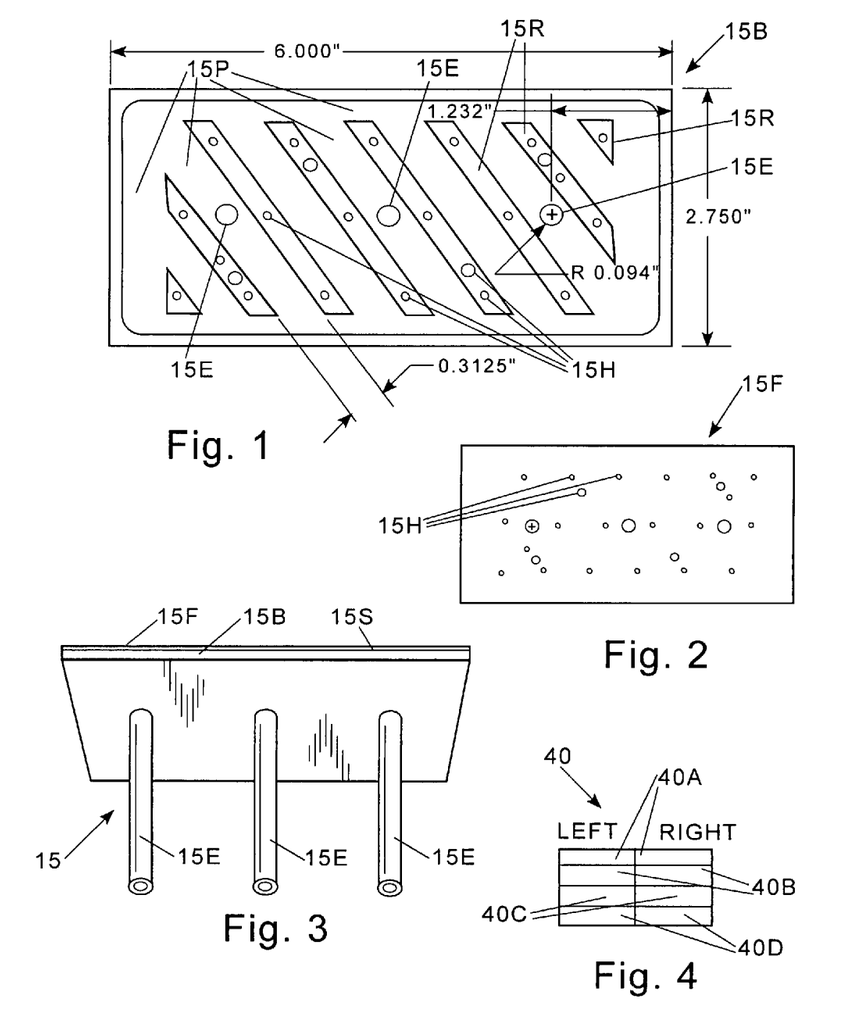
FIG. 1 is a side plan view of the inside of a rear component to a hollow flat plate of the present invention.
FIG. 2 is a side plan view of the outside of a front component to the hollow flat plate of FIG. 1.
FIG. 3 is a perspective view of a hollow flat plate of the invention having rear and front components as of FIGS. 1 and 2.
FIG. 4 is a side plan view of a multi-unit heating element array, which can be employed in the practice of the present invention such as in conjunction with the plate of FIG. 3.
Figure 5:
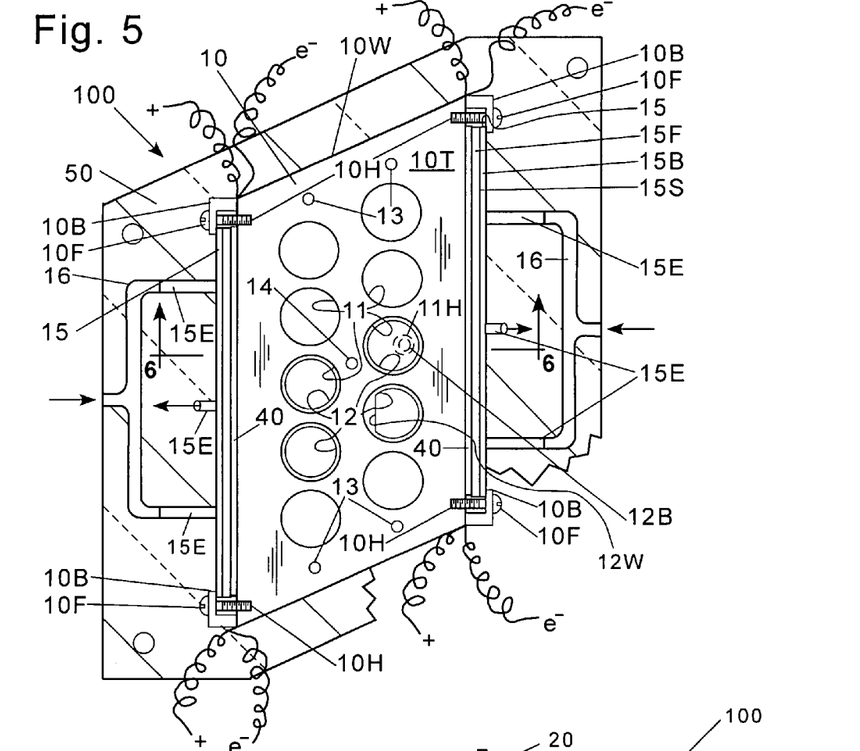
FIG. 5 is a top plan view of a block to which is mounted a pair of opposing hollow flat plates and corresponding arrays of heating elements as of FIGS. 3 and 4, respectively. The block contains a plurality of test cells, and has a rhomboid shape.
Figure 6:
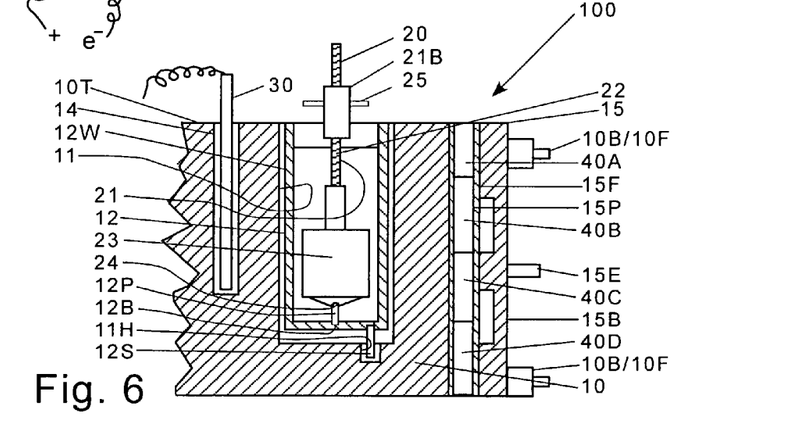
FIG. 6 is a sectional view of part of the ensemble of FIG. 5, taken generally through 6-6. To the same is added components for MRV/TP-1 testing such as a rotor with test drum, and so forth.
Figures 7, 8, 10A:
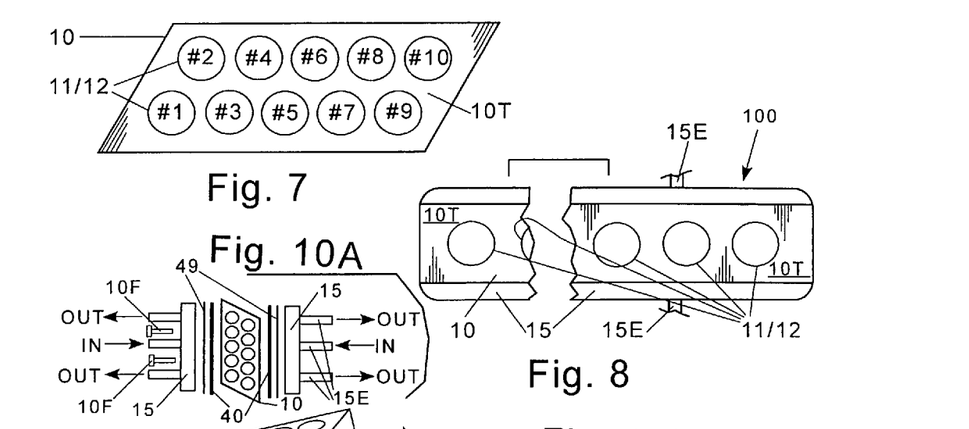
Figure 9:
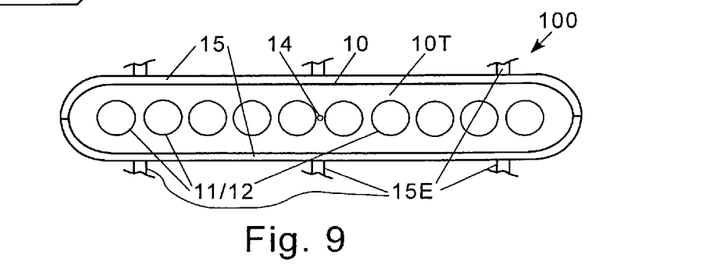

As alluded to above, the device 100 can provide highly accurate, precise and uniform temperature control. For example, in a test run of the device 100 of FIGS. 1-6, configured as an MRV device with the aluminum block 10 and with the machined 1/16" evaporators 15 with manifold 16, and with 1-inch diameter test ports 12 numerically identified as in FIG. 7, for 5W-30 test oil, the following data was obtained in degrees C.:

TABLE 1

CELL WALL TEMPERATURES

| | Set point | | | | | | | |
|---|---|---|---|---|---|---|---|---|
| | −5.0 | −10.0 | −15.0 | −20.0 | −25.0 | −30.0 | −35.0 | −40.0 |
| Cell #1 | −4.9 | −9.9 | −14.9 | −19.9 | −24.9 | −29.9 | −35.0 | −40.0 |
| Cell #2 | −5.0 | −10.0 | −15.1 | −20.0 | −25.1 | −30.1 | −35.0 | −40.0 |
| Cell #3 | −4.9 | −9.9 | −14.9 | −19.9 | −25.0 | −30.0 | −35.1 | −40.1 |
| Cell #4 | −5.0 | −10.0 | −15.0 | −20.1 | −25.1 | −30.1 | −35.0 | −40.1 |
| Cell #5 | −4.9 | −9.9 | −15.0 | −19.9 | −25.0 | −30.0 | −35.1 | −40.1 |
| Cell #6 | −5.0 | −10.0 | −15.1 | −20.1 | −25.0 | −30.0 | −35.0 | −40.1 |
| Cell #7 | −5.0 | −10.1 | −15.1 | −19.9 | −25.0 | −30.0 | −35.1 | −40.0 |
| Cell #8 | −4.9 | −10.1 | −15.0 | −20.0 | −25.1 | −30.1 | −35.1 | −40.0 |
| Cell #9 | −5.0 | −10.0 | −15.1 | −20.1 | −25.1 | −30.1 | −35.0 | −40.0 |
| Cell #10 | −5.1 | −10.0 | −15.0 | −20.0 | −25.1 | −30.0 | −35.0 | −40.1 |

TABLE 2

DEVIATION FROM SET POINT

| | Set point | | | | | | | |
|---|---|---|---|---|---|---|---|---|
| | −5.0 | −10.0 | −15.0 | −20.0 | −25.0 | −30.0 | −35.0 | −40.0 |
| Cell #1 | 0.1 | 0.1 | 0.1 | 0.1 | 0.1 | 0.1 | 0.0 | 0.0 |
| Cell #2 | 0.0 | 0.0 | −0.1 | 0.0 | −0.1 | −0.1 | 0.0 | 0.0 |
| Cell #3 | 0.1 | 0.1 | 0.1 | 0.1 | 0.0 | 0.0 | −0.1 | −0.1 |
| Cell #4 | 0.0 | 0.0 | 0.0 | −0.1 | −0.1 | −0.1 | 0.0 | −0.1 |
| Cell #5 | 0.1 | 0.1 | 0.0 | 0.1 | 0.0 | 0.0 | −0.1 | 0.0 |
| Cell #6 | 0.0 | 0.0 | −0.1 | −0.1 | 0.0 | 0.0 | 0.0 | −0.1 |
| Cell #7 | 0.0 | −0.1 | −0.1 | 0.1 | 0.0 | 0.0 | −0.1 | 0.0 |
| Cell #8 | 0.1 | −0.1 | 0.0 | 0.0 | −0.1 | −0.1 | −0.1 | 0.0 |
| Cell #9 | 0.0 | 0.0 | −0.1 | −0.1 | −0.1 | −0.1 | 0.0 | 0.0 |
| Cell #10 | −0.1 | 0.0 | 0.0 | 0.0 | −0.1 | 0.0 | 0.0 | −0.1 |

This shows that deviations from set points of −0.1 to 0.1 degrees C. across the length and breadth of the test block 10 can be obtained. Excellent temperature control thus can be provided.

Figures 10B, 11A, 11B:
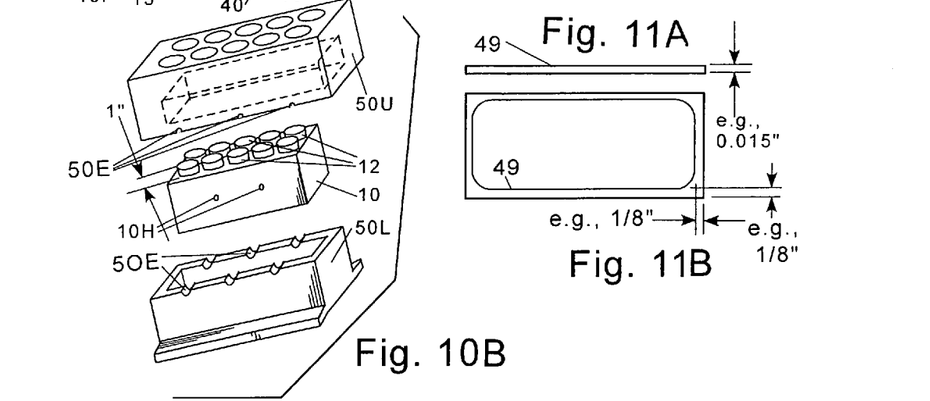

Even better control can be provided by thermally insulating spacer 49 set against the heater 40, which can temper the effect of an irregular/uneven cold heat sink/evaporator plate 15. The device 100 can have convection/radiation between the plate 15 and block 10 and conduction between the heater 40 and the block 10. See, e.g., FIG. 10 et seq.

Further, with respect to the drawings, the following is noted, particularly with respect to FIG. 10 et seq.:

Upper insulation 50U and lower insulation 50L cover the test block 10 with the heater 40, a spacer 49, and the evaporator 15. The spacer 49 can be 0.015" thick. Refrigerant flow goes in and out the ports 15E. Bolts 10F can fasten the evaporator 15, spacer 49 and heater 40 to the test block via bolt holes 10H. The upper insulation 50U locates on cell inserts, which create test cells and stick up about an inch. The seam of the insulation 50L and 50U is at the center of the block 10, and holes 50E have a ½-inch diameter to allow refrigerant lines 15E to come out. The spacer 49 creates a boundary layer for the heat and cool to mix prior to getting to the test block 10. This evens out the cooling surface. The block profile is made lower. Compare, FIGS. 10A and 10B.

The spacer 49, too, is the same basic shape as the heater 40 and evaporator 15. The spacer, for example, can be 0.015" thick TEFLON polytetrafluoroethylene "gasket" material. The thickness may change for other applications. Inside area of the spacer 49 can be open, and inside corners could be a radius or any shape which may help with strength or thermal transfer/impedence. Compare, FIGS. 11A and 11B.

Figures 12, 13A, 13B, 14, 15A, 15B:
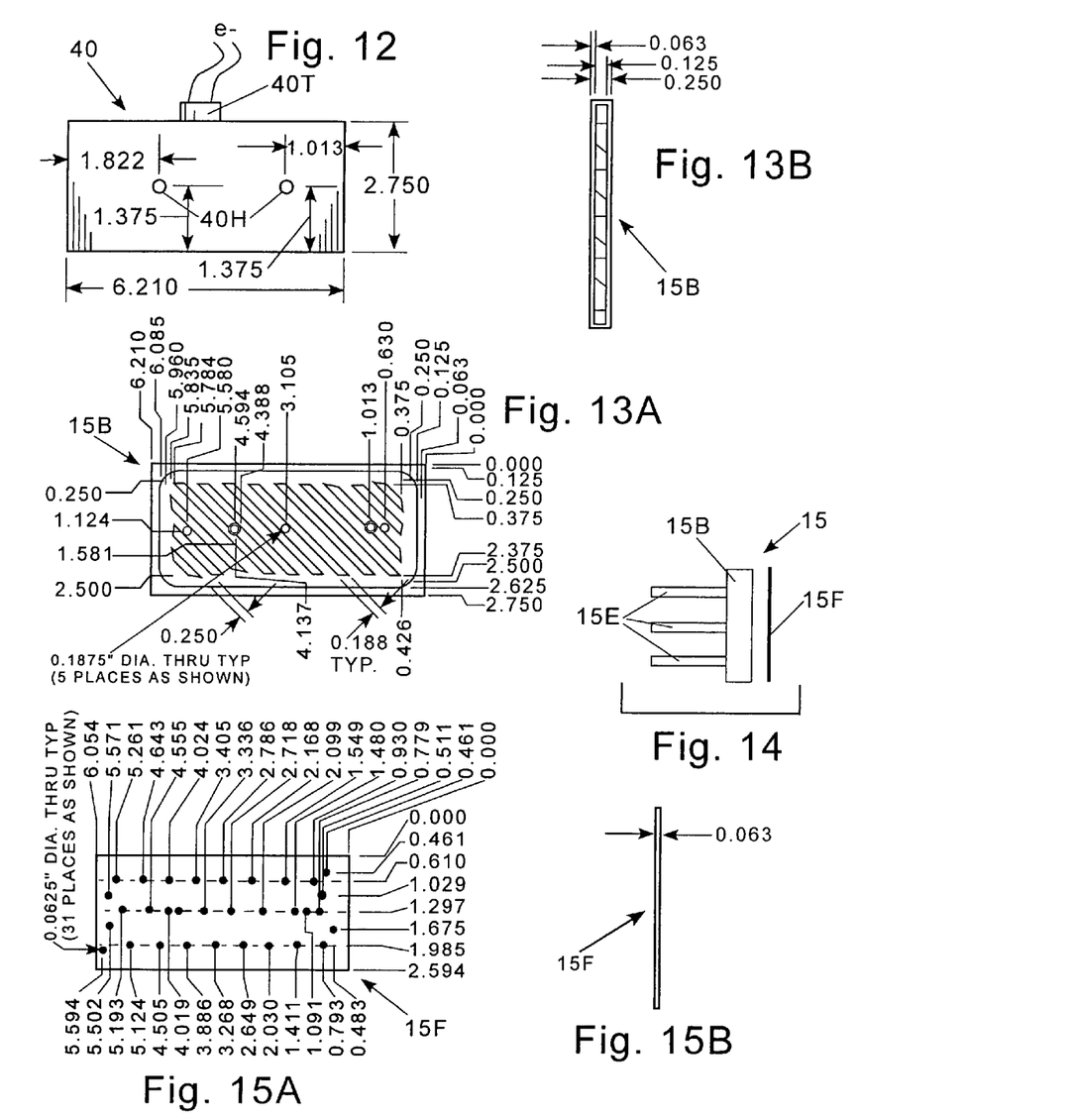

The heater 40 can be a 120-volt AC, 170-watt polymide KAPTYN thin film heater, with a termination tab centered along the top edge. Two 0.25-inch diameter holes 40H go through and PSA adhesive goes on the front side of the heater. Compare, FIG. 12.

The evaporator back 15B can be free-machining copper. It can have a rail along its four outer boundaries 0.125" wide, with 0.063-inch radii at the four corners. Compare, FIGS. 13A and 13B.

The evaporator halves, front 15F and back 15B, get soldered together to create a series of openings, grooves, channels, and open space. Compare, FIG. 14.

The evaporator front 15F can be free-machining copper. It also can have 0.063-inch radii at the four corners. Compare, FIGS. 15A and 15B.

Figures 16A, 16B:
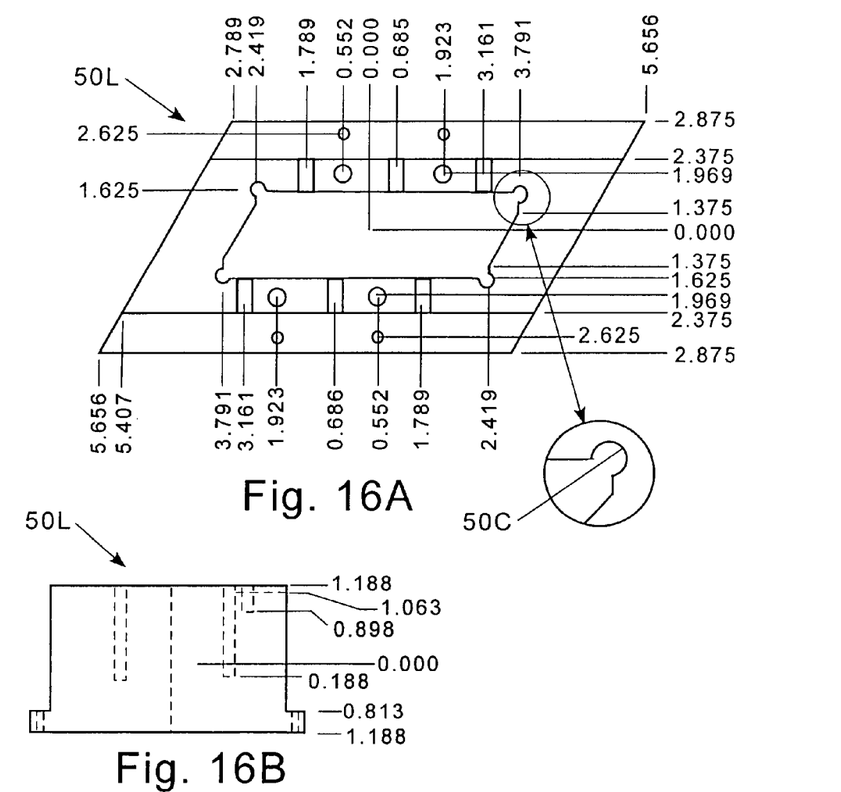
Figure 16C:
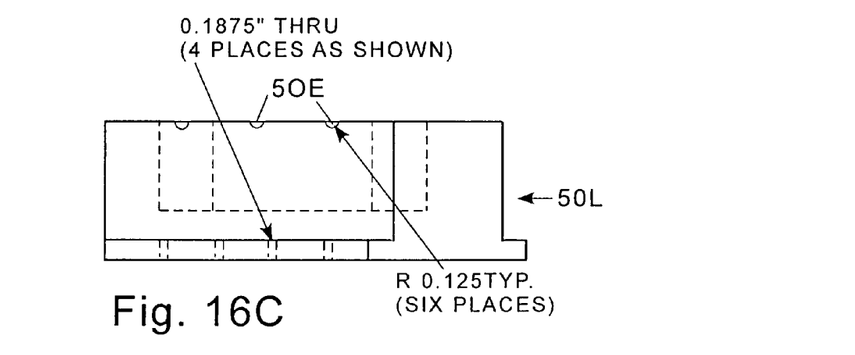

The lower block insulation 50L, for example, is SYNTAC 350 foam composite. Holes at 0.552 and 1.923 are oriented vertically. Four corners 50C are relieved with a ⅛-inch diameter cutter. Compare, FIGS. 16A, 16B and 16C.

Figure 17A:
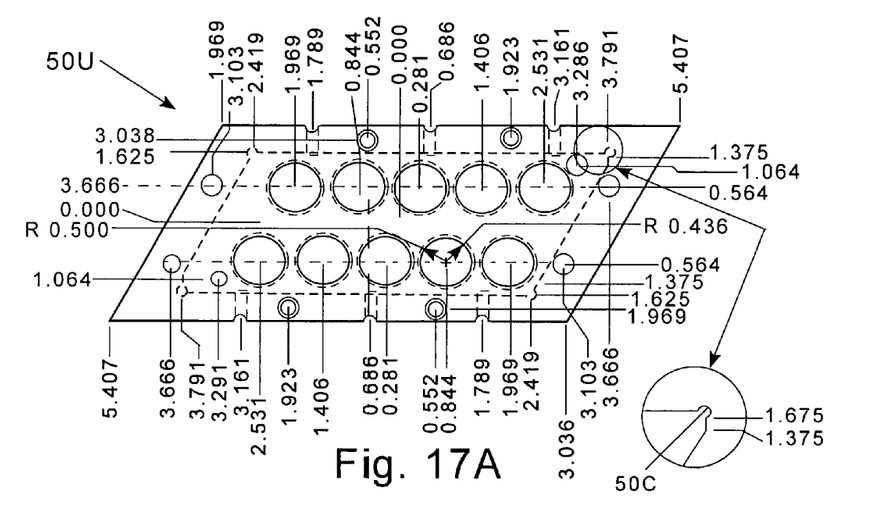
Figure 17B:
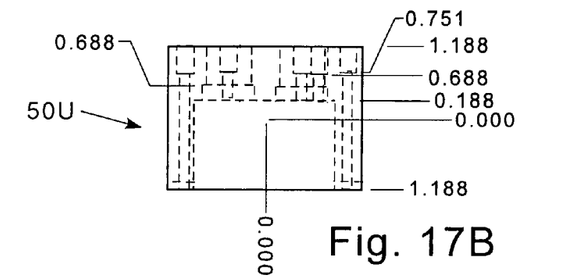
Figure 17C:
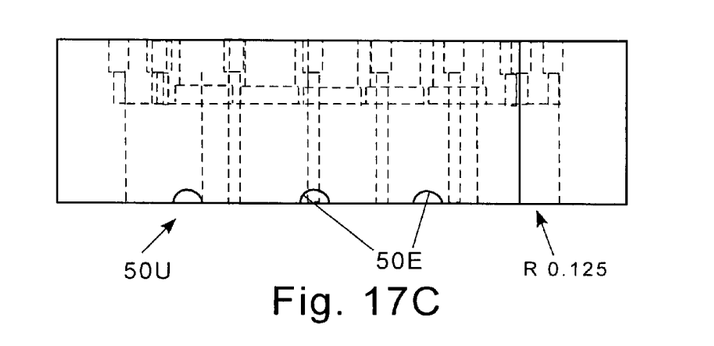

The upper block insulation 50U, for example, is SYNTAC 350 foam composite. The hole halves 50E at 1.789, 0.686 and 3.161 are oriented horizontally, with full holes oriented vertically. Again, the four corners 50C are relieved with a ⅛-inch diameter cutter. Compare, FIGS. 17A, 17B and 17C.

Figures 18A, 18B, 19A, 19B, 19C, 19D, 19E:
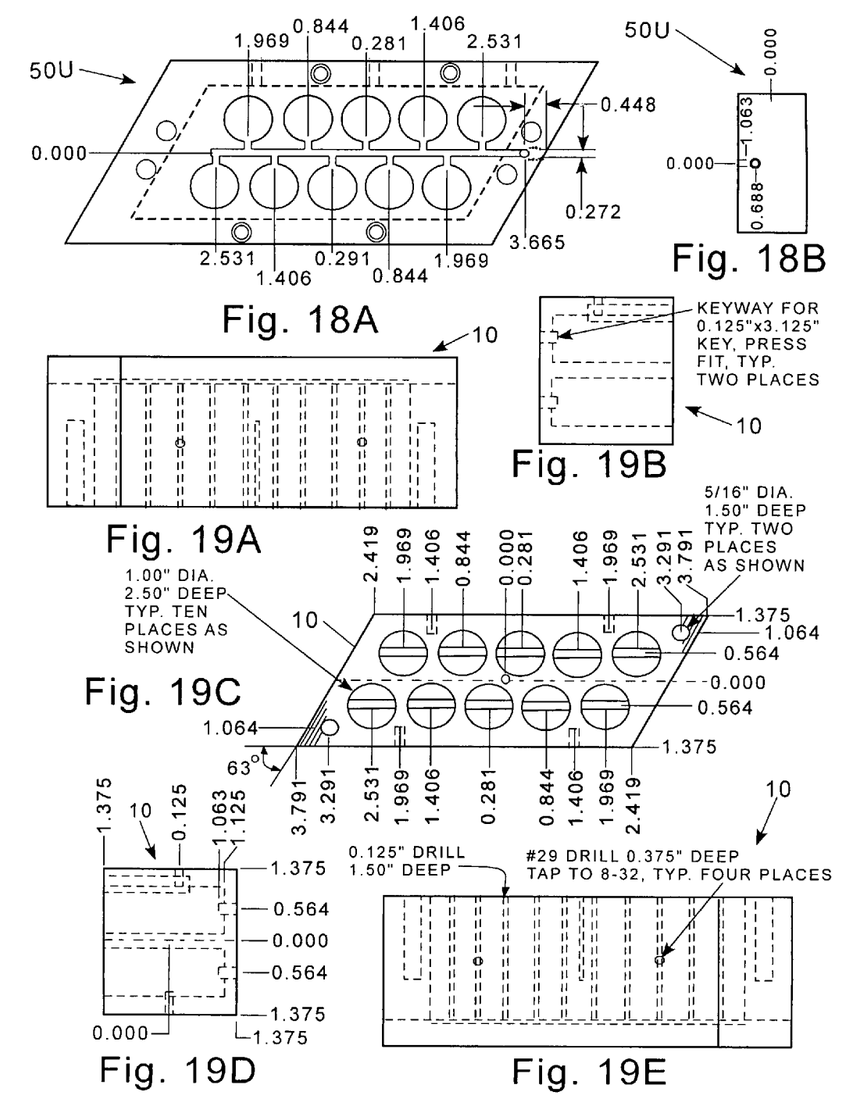

An air delivery system is additionally machined into the top of the upper block insulation 50U, for example, of the SYNTAC 350 foam composite. A 0.125" wide groove, 0.125" deep, is provided along a centerline. The groove must break into the centerline of the ten test port holes. A 0.125" hole is drilled at 3.665. Compare, FIGS. 18A and 18B (many hidden lines omitted for clarity).

SYNTAC 350 is a syntactic foam available from Emerson & Cuming Composite Materials, Inc., Canton, Mass. Generically, it is a rigid high-strength composite of epoxy resin and microscopic hollow glass microspheres, easily machined using standard shop tools, with low thermal conductivity. It has a 17×10-to-the-minus-6th in./in. degree F. coefficient of thermal expansion; a 0.07 BTU/hr./sq. ft./degree F./thermal conductivity; a 0.50 BTU/lb./degree F. specific heat; a 6,500-psi compressive strength; a 3,000-psi shear strength; a 350-degree F. service temperature; and a 55-unit shore D hardness. Note, FIGS. 16A, 16B, 16C, 17A, 17B, 17C, 18A and 18B.

The block 10 is made of 6061-Aluminum. Compare, FIGS. 19A, 19B, 19C, 19D and 19E.

Numeric values hereof may be considered exact or approximate.

The present invention is thus provided. Various feature(s), part(s), step(s), subcombination(s) and/or combination(s) can be employed with or without reference to other feature(s), part(s), step(s), subcombination(s) and/or combination(s) in the practice of the invention, and numerous adaptations and modifications can be effected within its spirit, the literal claim scope of which is particularly pointed out as follows:

What is claimed is:

1. In combination:

A hollow type plate through which refrigerant gas can pass, which can be employed for refrigeration of a block by employment of the plate in thermal communication with the block but not by communication of the refrigerant gas between the plate and interior of the block; and the block, wherein the plate is positioned adjacent the block such that the refrigeration of the block can be carried out as aforesaid.

2. The combination of claim 1, wherein the plate is a flat type plate having a first wall having a substantially laterally extensive portion opposing a second wall having a substantially laterally extensive portion with a hollow portion between the substantially laterally extensive portions of the first and second walls between which the refrigerant gas can pass and wherein distance between the substantially laterally extensive portions of the first and second walls is substantially less than distances that the substantially laterally extensive portions of the first and second walls laterally extend.

3. The combination of claim 1, wherein the plate can withstand 7,500 pounds total force at 500 psi.

4. The combination of claim 2, wherein the plate can withstand 7,500 pounds total force at 500 psi.

5. The combination of claim 4, wherein the block contains test cell(s) for testing of viscosity/rheology of a fluid.

6. The combination of claim 5, which contains a heater.

7. The combination of claim 6, wherein:

the block is equipped with side mounting brackets and mounting fasteners; and has a top;

the test cell(s) are substantially cylindrical;

a temperature sensor is present;

the plate is configured to outer boundaries of opposing long sides of the block in a form of a pair of plates, each plate being essentially equivalent in size and shape with respect to the other plate;

the heater is in a form of at least one thin film electric heating element; and insulation is provided to generally surround the block.

8. The combination of claim 7, wherein the heater is present between the plate and the block, and the heater is spaced from the plate with a thermally insulating material.

9. The combination of claim 5, wherein the block has a rhomboid shape.

10. The combination of claim 8, wherein the block has a rhomboid shape, and the plates are substantially planar.

11. The combination of claim 5, wherein the block is elongated in a first direction and has one and only one row of a plurality of test cells that extend along the first direction; and the plate is configured to outer boundaries of the block.

12. The combination of claim 11, wherein the block has two rounded ends; and the plate is provided in a form of two opposing plate sections that span substantially along the first direction along long sides of the block, each plate being essentially equivalent in size and shape with respect to the other plate.

13. A rhomboid shaped TP-1 type test block with test wells, wherein the test wells are provided in a plurality of rows with individual test wells in a row offset from individual test wells in another row such that a rhomboid array of test wells is provided in the block.

14. The test block of claim 13, wherein there are two rows of the test wells.

15. A hollow type plate through which refrigerant gas can pass, which comprises a flat type plate having a first wall having a substantially laterally extensive portion with a hollow portion between the substantially laterally extensive portions of the first and second walls between which the refrigerant gas can pass and wherein the distance between the substantially laterally extensive portions of the first and second walls is substantially less than distances that the substantially laterally extensive portions of the first and second walls laterally extend; and an inlet and an outlet for the refrigerant gas, such that the plate can be employed for refrigeration of a block by employment of the plate in thermal communication with the block by passing the refrigerant gas through the hollow type plate and wherein said plate is provided in a form of a central section formed of two opposing wall portions that span substantially planarly; and two opposing end sections, each of which is formed of two curving wall sections that curve in a same first direction away from the central section.

16. The combination of claim 2, wherein the plate is substantially planar.

17. The combination of claim 4, wherein the plate is substantially planar.

18. The combination of claim 5, wherein the plate is substantially planar.

19. The combination of claim 6, wherein the plate is substantially planar.

20. The combination of claim 9, wherein the plate is substantially planar.

* * * * *